United States Patent [19]

Berends

[11] Patent Number: 5,377,000

[45] Date of Patent: Dec. 27, 1994

[54] PORTABLE APPEARANCE MEASURING APPARATUS

[75] Inventor: David C. Berends, Pennington, N.J.

[73] Assignee: Color and Appearance Technology, Inc., Princeton, N.J.

[21] Appl. No.: 53,680

[22] Filed: Apr. 29, 1993

[51] Int. Cl.$^5$ .................. G01J 3/51; G01N 21/27; G01N 21/57

[52] U.S. Cl. .................... 356/73; 356/407; 356/419

[58] Field of Search .............. 356/73, 446, 419, 402, 356/407, 416, 328

[56] References Cited

U.S. PATENT DOCUMENTS

| | | | |
|---|---|---|---|
| 3,890,049 | 6/1975 | Collins et al. | 250/559 X |
| 4,040,743 | 8/1977 | Villaume et al. | 356/73 |
| 4,101,222 | 7/1978 | Mathisen | 356/402 X |
| 4,218,144 | 8/1980 | Whitehouse et al. | 356/446 |
| 4,222,064 | 9/1980 | Lodzinski | 356/73 |
| 4,239,393 | 12/1980 | Tobias | 356/407 |
| 4,464,054 | 8/1984 | Karras et al. | 356/406 |
| 4,669,873 | 6/1987 | Wirz | 356/73 |
| 4,678,325 | 7/1987 | Lehtikoski et al. | 356/73 |
| 4,830,504 | 5/1989 | Frohardt et al. | 356/448 |
| 4,886,355 | 12/1989 | Keane | 356/73 |
| 4,937,764 | 6/1990 | Komatsu et al. | 356/446 X |
| 4,968,143 | 11/1990 | Weston | 356/328 |

OTHER PUBLICATIONS

Metrologia by Springer-Verlag 1980, "A Reference Instrument for 20°, 60° and 85° Gloss Measurements", by W. Budde, pp. 1–5 (1980).

Primary Examiner—Vincent P. McGraw
Attorney, Agent, or Firm—Mathews, Woodbridge & Collins

[57] ABSTRACT

A hand-held combined spectrophotometer and gloss meter quickly and effectively measures the appearance of a color sample. Light generated by a krypton-filled tungsten bulb shines on the sample and is reflected at 45° into twenty-one photodiodes spaced at staggered intervals around the sample stage. A diffuser in the light path reflects a portion of the light back onto a pair of red and blue sensitive reference photodiodes. The output of the red and blue reference diodes compensates for changes in the output of the bulb. An LED produces light which shines on the color sample at an angle of 30°. The reflected light is received by a large-area photodetector which determines the gloss of the sample. A viewing port permits the user to view the sample prior to measurement. When the viewing port door is opened, it automatically actuates the light and illuminates the sample for viewing. The viewing port door is automatically closed by a return spring. The instrument can be hand-held and operated by buttons on the front or a redundant button on the back. The operator may choose between a simple pass/fail appearance indication or can obtain more detailed information from an LCD display. The instrument may also be mounted for lab use and connected to exterior peripherals such as printers and the like.

14 Claims, 15 Drawing Sheets

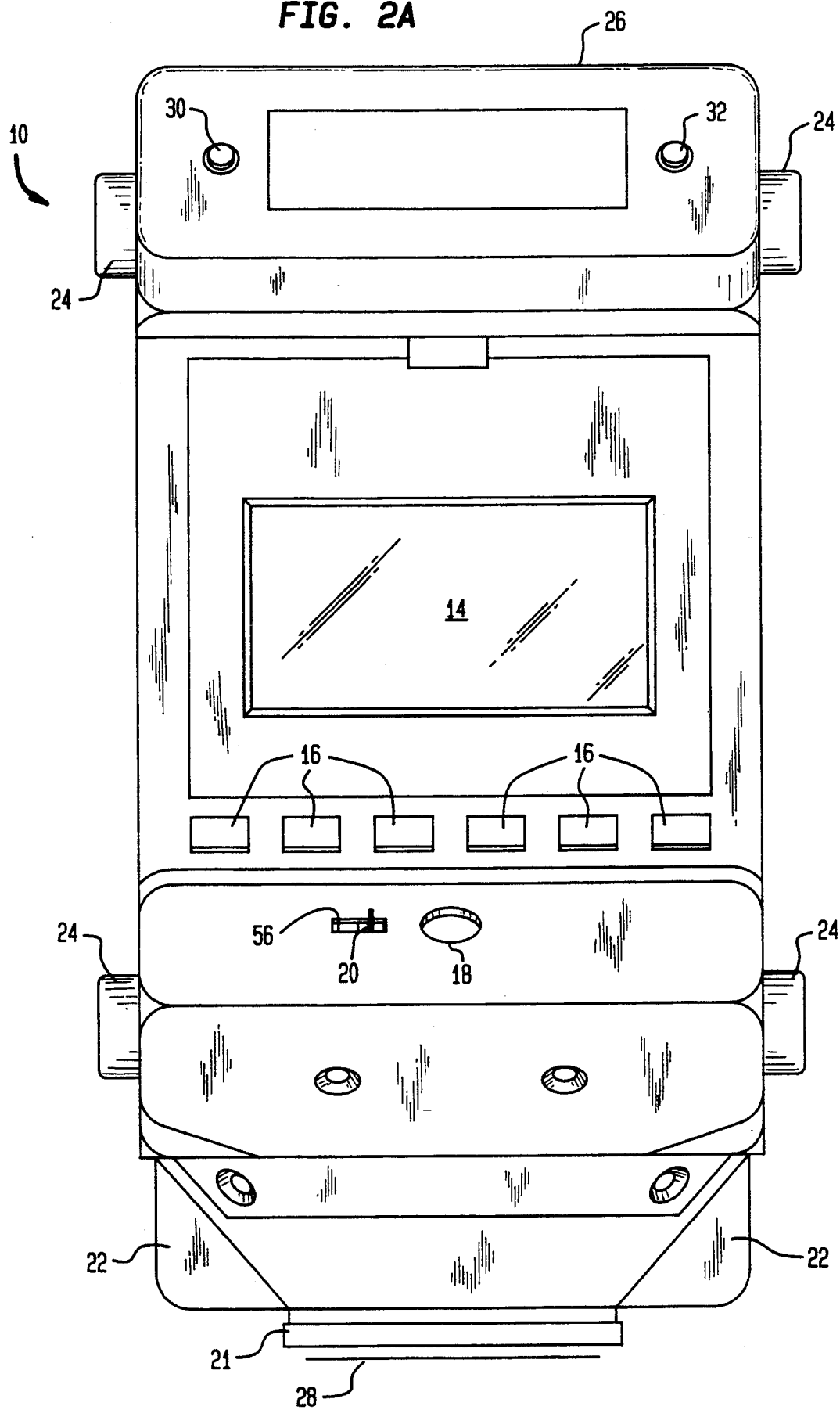

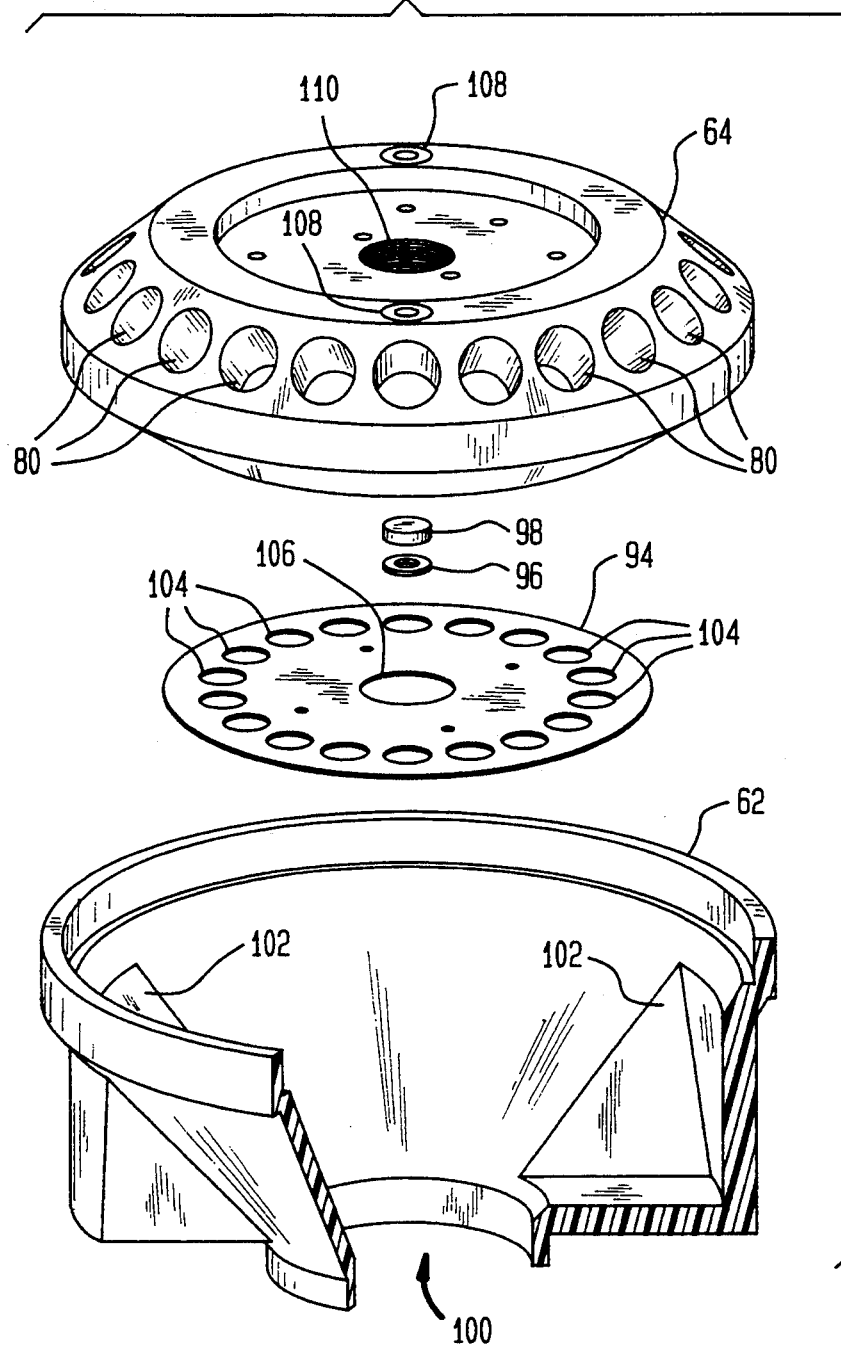

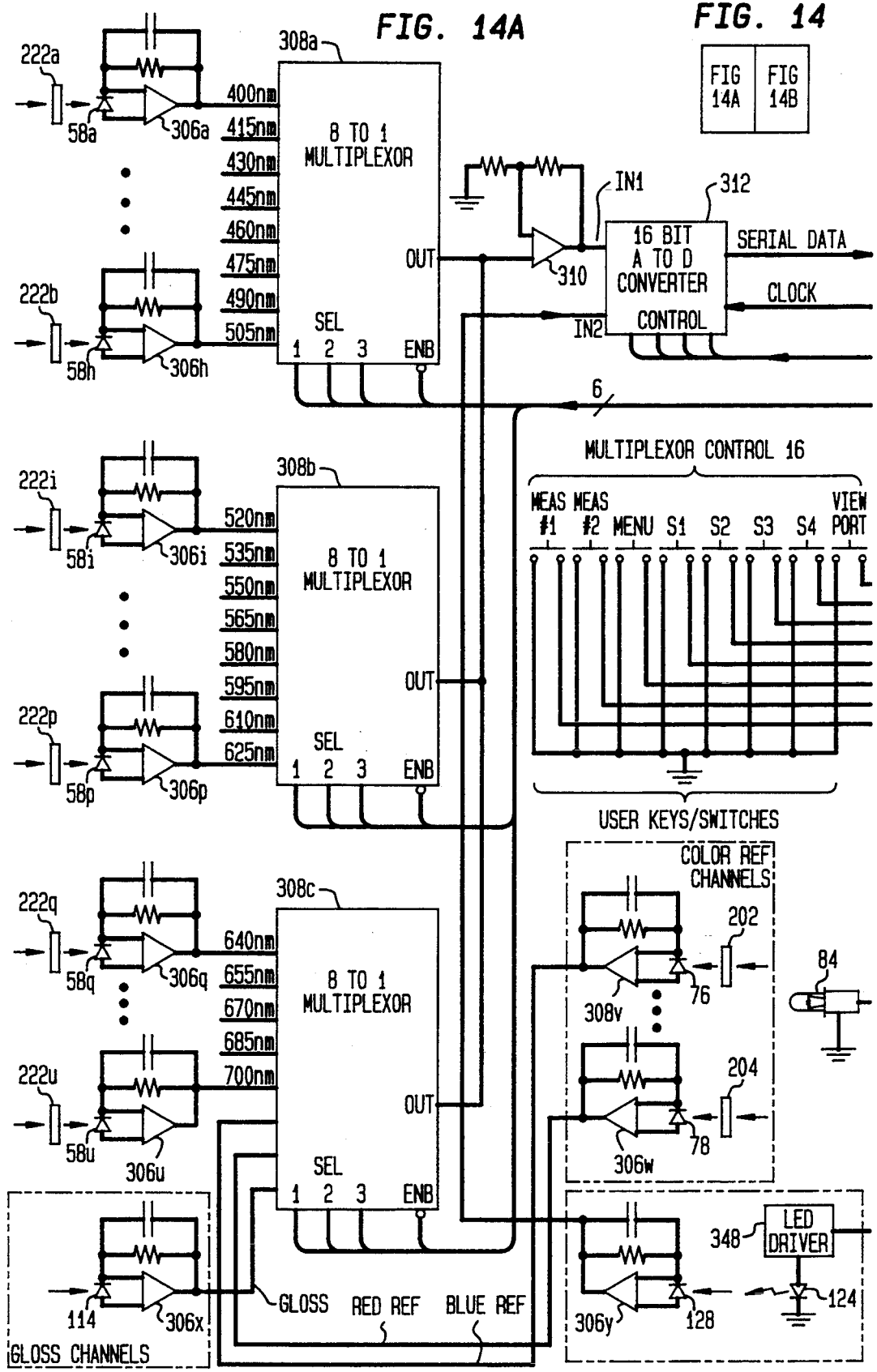

PORTABLE APPEARANCE MEASURING APPARATUS

BACKGROUND OF THE INVENTION

1. Field of the Invention

The invention comprises a hand-holdable combined spectrophotometer and gloss meter for measuring the appearance of a colored sample.

2. Description of Related Art

A few hand-holdable spectrophotometers have been in existence on the market since the late 1980s, but have yet to penetrate the marketplace significantly due to numerous factors, including high cost, lack of ruggedness, inadequate performance and weak human ergonometric factors. Much of the prior art instrumentation is aimed at limited segments of the color marketplace, such as graphic arts spectrometers which are based on older densitometer package designs. Much of the prior art instrumentation is also highly directional. In bi-directional instruments, i.e. those with 0°/45° geometry, either the illumination system or the detection system, and preferably both, have to be very uniform and symmetric. If not, directional samples, such as corduroy fabrics, will produce significantly different measurements depending upon their rotational orientation with respect to the instrument.

Another problem with prior art hand-held spectrophotometers is that they often used pulsed xenon lamps which have an astable line structure in their output power spectra. While it is possible to use incandescent lamps due to their inherently higher stability, nevertheless, they suffer from deterioration over time and variation from measurement to measurement.

The prior art patent literature describes recent efforts to integrate color and gloss measurements into the same instruments. In particular, U.S. Pat. No. 4,678,325 entitled APPARATUS FOR MEASURING OPTICAL PROPERTIES OF PAPER issued on Jul. 7, 1987 discloses a fairly large instrument that appears to be capable of measuring both color and gloss. U.S. Pat. No. 4,886,355 entitled COMBINED GLOSS AND COLOR MEASURING INSTRUMENT issued on Dec. 12, 1989 describes a device that employs fiber optic bundles for the purpose of gathering gloss and color information from the sample. While such an approach has advantages, it also has its disadvantages, too, namely that adds additional elements to the instrument. Other prior art patents that may be relevant to the use of fiber optic bundles in the context of color and/or gloss measuring instruments include: U.S. Pat. Nos. 3,890,047; 4,040,743; 4,218,144; 4,222,064; 4,646,054; and 4,669,873. Also of possible relevance is an article entitled A REFERENCE INSTRUMENT FOR 20° 60° AND 85° GLOSS MEASUREMENTS which appeared in Metrologia, by Springer-Verlag, Volume 16, pp 1-5, 1980.

Other U.S. patent references of possible relevance include: U.S. Pat. Nos. 3,890,049; 4,040,743; 4,218,144; 4,319,847; 4,464,054; 4,669,873; 4,678,325; 4,886,355.

The prior art does not appear to disclose a reliable hand-held combined spectrophotometer and gloss meter which is easy to use, rugged, and provides accurate, reliable measurements of sample appearance.

SUMMARY OF THE INVENTION

Briefly described, the invention comprises a hand-held combined spectrophotometer and gloss meter capable of making efficient and accurate measurements of the appearance of a sample surface. The instrument generates uniform and symmetrical illumination of the sample surface area, thereby allowing the mechanical combination of the instrument's monochromating and light collecting functions without affecting the instrument's measurement capability on highly directional samples. An incandescent krypton-filled tungsten lamp is used as the light source. It has been determined that substantially the entire spectral power distribution (SPD) of krypton incandescent lamps can be accurately predicted from measurements of two spectral points at the extreme ends of the visible spectrum. The present invention makes use of this relationship by measuring light at 400 nm and at 700 nm and using that information to compensate for variations in illumination from the krypton light source. This obviates the need for an entire monochromating system dedicated to characterizing the lamp SPD as might be the case with Xenon lamps used in the prior art.

The entire instrument is housed in a case. Located on the outside of the case are an LCD display, a plurality of operational keys, a pair of pass/fail LED lights, a battery cover case, a sample viewing port and slide opener, an RS-232 cable connector on the back, a redundant operational button on the backside of the case, two pairs of laboratory mounts (one pair on each side) and a bottom sample port. Twenty-one photodetectors are arranged in an annular ring and pointed to receive light reflected at an angle of 45° from the surface of the object being measured. The color photodetectors detect a light in 15 nm intervals between 400 nm and 700 nm. Each color photodetector is staggered with respect to its nearest neighbor so that each photodetector is significantly more than 15 nm from adjacent photodetectors. This helps to insure that the instrument is not preferential in orientation. The annular housing also includes a light emitting LED and a large surface photodiode arranged at an angle of 30° with respect to the surface of the sample for measuring 60° gloss.

The operator of the instrument can view the surface of the sample through a sample viewing port in the side of the instrument. To open the port, the operator moves a slide which simultaneously actuates a limit switch to illuminate the sample inside of the instrument. Therefore, the operator can view the actual sample from the same perspective as the twenty-one photodiodes. When the operator removes his or her finger from the slide, it automatically closes under the influence of a spring and the viewing light is turned off.

The present unit fits comfortably into the hand of either a left or right-handed user. The case includes two protruding ledge-like regions at the units top, one in the front and one in the back, against which the user's thumb and middle finger are placed. The unit's backside is curved to comfortably to fit the contour of the fingers of both large and small hands. Measurement initiation is easily effected by the index finger of either hand. The instrument weighs approximately two pounds which makes it considerably lighter than prior art alternatives. A highly impact resistant plastic case and rugged interior structure make it capable of withstanding routine abuse. In addition to being hand-holdable, the unit can also be mounted on a bench top stand which permits the operator to repeat extremely highly accurate, vibration free measurements in a laboratory setting. Finally, the structure of the invention makes it relatively easy for the operator to replace the krypton-filled tungsten lamp. In summary, the unit is relatively small, rugged, easy to use and extremely accurate in its measurement of color and gloss.

These and other features of the invention will be more fully understood by reference to the following drawings.

BRIEF DESCRIPTION OF THE DRAWINGS

FIG. 2A is a front elevational view of the instrument.

FIG. 7 is an exploded view of the main color detector and filter housing, annular aperture ring and lower outer cone of the color head measurement assembly of FIGS. 4 and 5.

FIGS. 14A and 14B comprise a schematic diagram illustrating the electronic components that control the preferred embodiment of the instrument and their relationship to the elements illustrated in FIGS. 1–13B above.

DETAILED DESCRIPTION OF THE PREFERRED EMBODIMENT

During the course of this description, like numbers will be used to identify like elements according to the different views that illustrate the invention.

Figure 1:
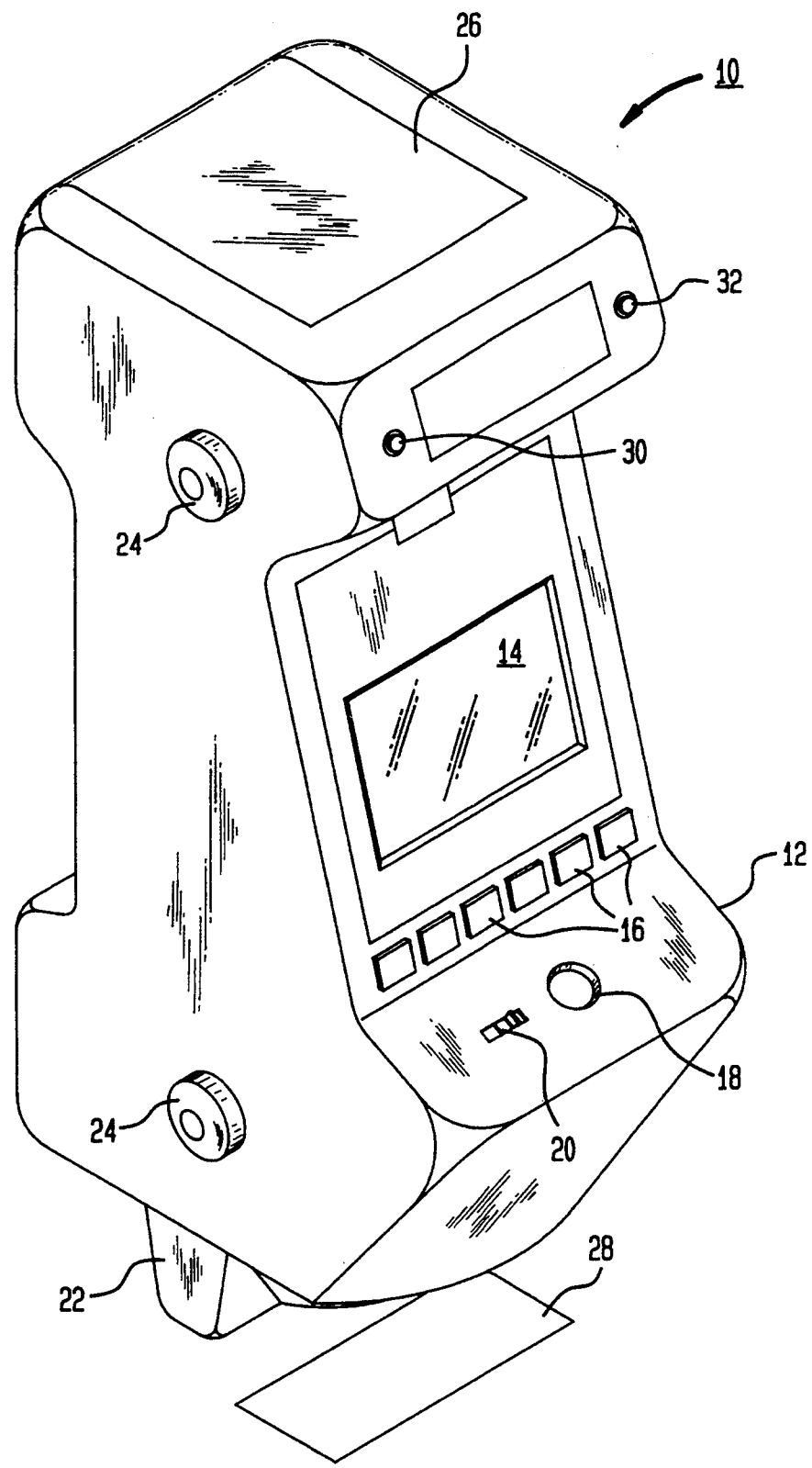
FIG. 1 is a front perspective view of the preferred embodiment of the appearance measuring instrument.
Figure 2B:
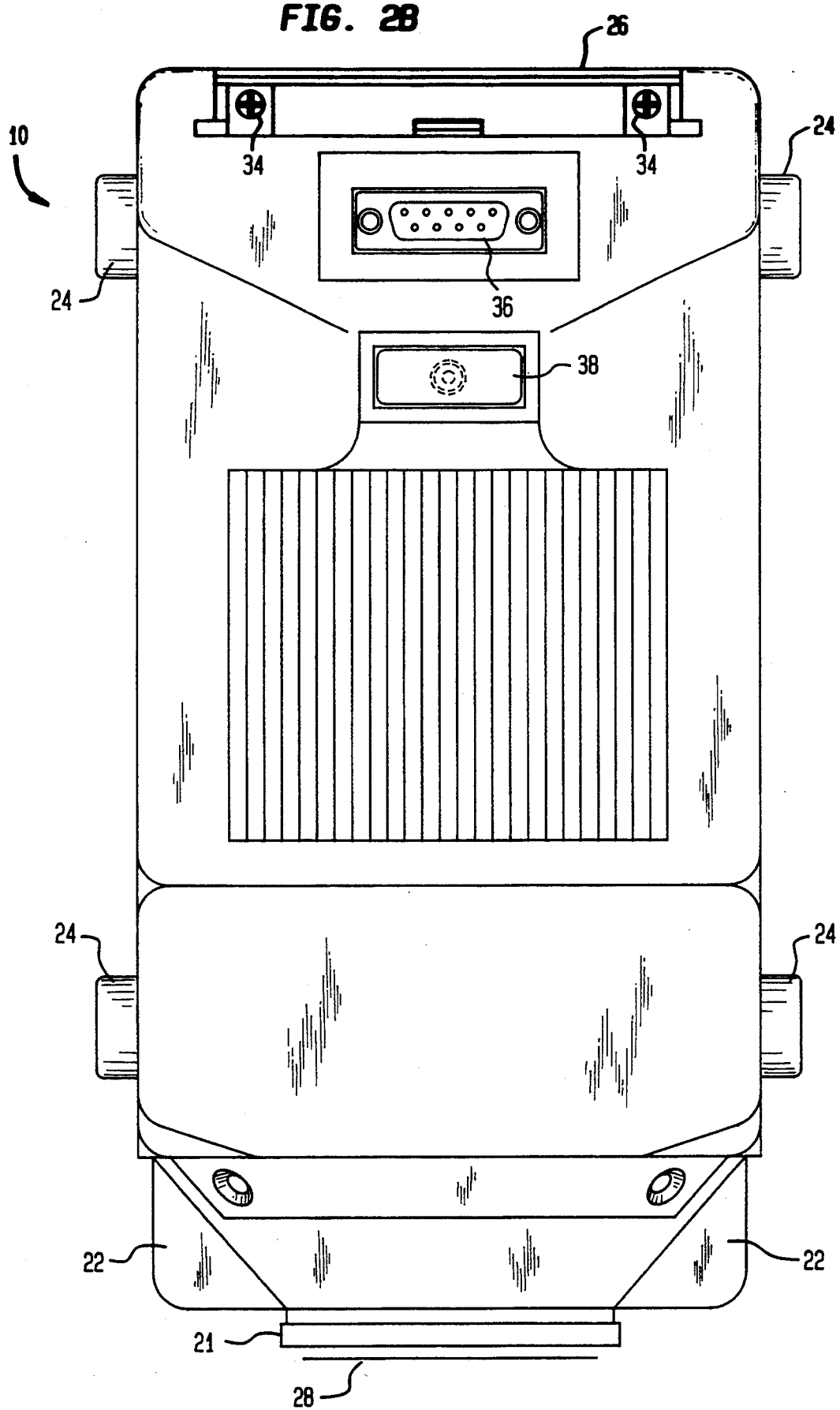
FIG. 2B is a rear elevational view of the instrument.

The exterior features of the preferred embodiment 10 of the invention are best understood by referring to FIGS. 1, 2A and 2B. An exterior case or chassis 12, preferably comprising a front half and a rear half, forms the skin around the instrument 10. Output data is visible on a liquid crystal data display (LCD) 14. User keys 16 provide instructions to the instrument 10. Preferably, the key on the far left initiates the measurement process and the remaining keys call for a variety of specific measurements.

A viewport 18, which can be selectively opened and closed by means of slide mechanism 20, permits the user to selectively view a test sample 28 prior to or immediately following test measurements. Details of the viewport 18 mechanism are described subsequently with respect to FIGS. 9A and 9B. The test sample 28 is typically located within the opening 100 under the lower annular ring 21 which is selectively attachable to the conical bottom section 62 of the light measuring head assembly 60. A pair of sideways projecting protuberances 22 house the emitter and the detector portions of the gloss measuring sub-assembly 112. Four laboratory bench stand mounts 24 permit the instrument 10 to be firmly attached to an appropriate stand in order to improve the accuracy and repeatability of the instrument 10 free from vibration. Two lab mounts 24 are located on the left side of the instrument 10 and two are located in corresponding positions on the right side of the instrument 10 as shown clearly in FIGS. 2A and 2B. A battery cover 26 is located on the top of the case 12 and permits selective access to the battery compartment. The instrument 10 can be run by six (6) internal AA NiMH (Nickel Metal-Hydride) batteries, or their equivalent, if hand-held operation is desired. See battery pack 330 schematically illustrated in FIG. 14B. Alternatively, the instrument 10 can be powered from an exterior source 350 also illustrated in FIG. 14B. A pair of battery compartment screws 34, visible in FIGS. 2B and 3, help to hold the internal components together.

For quick measurements, LED pass and fail lights 50 and 32, respectively, can be employed. Measurement initiation can be activated either by the button 16 on the far left as illustrated in the front view of FIG. 2A or by pushing button 38 on the rear side of the instrument 10 as illustrated in FIG. 2B. Actuation of either button can cause the instrument to perform a pass/fail test, the results of which are indicated by LEDs 30 or 32. Alternatively, more sophisticated data can be provided via LCD display 14. The instrument 10 can also be connected to a computer or other peripheral, such as a printer, via RS-232 computer cable female plug 36.

Figure 3:
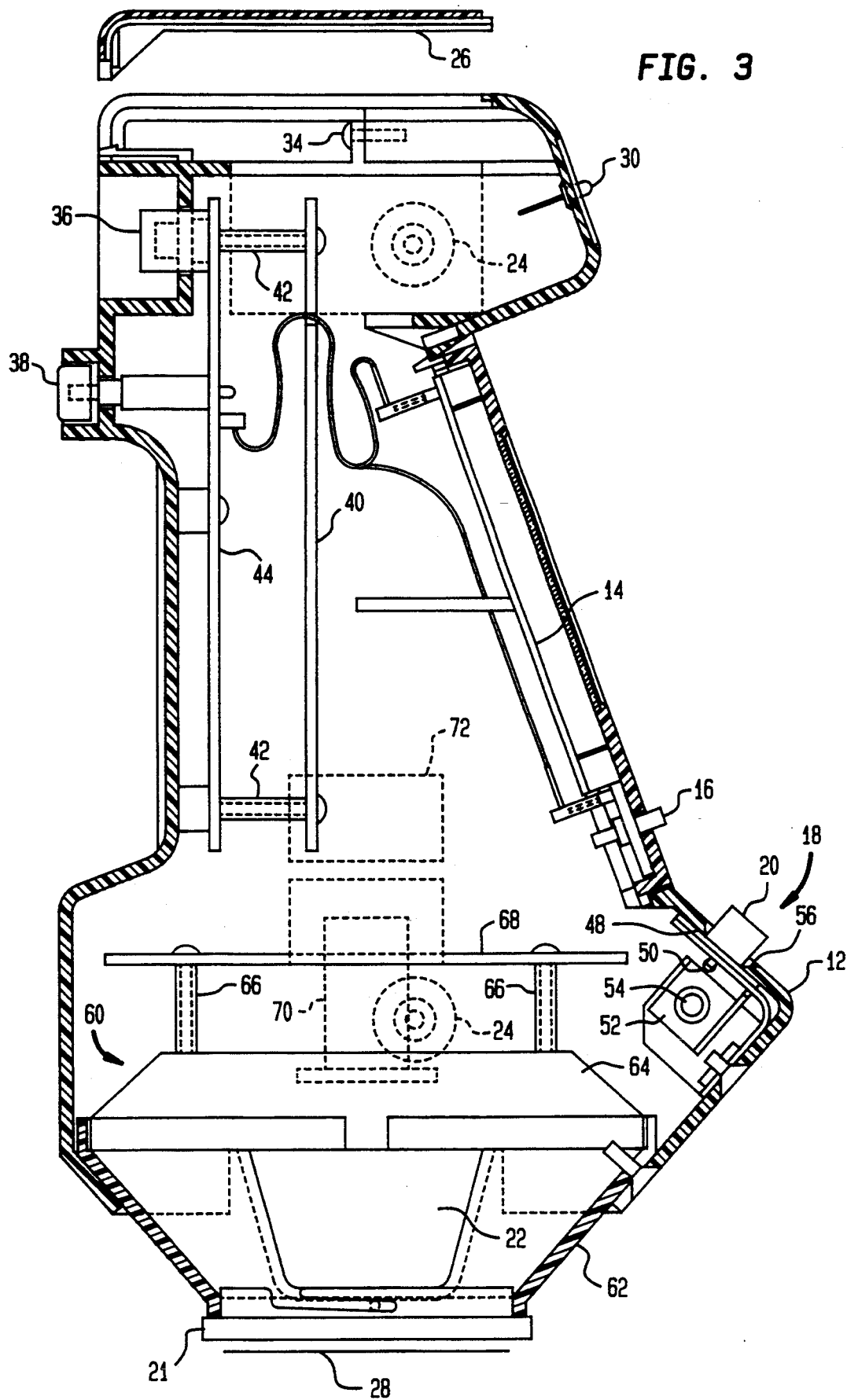
FIG. 3 is a left side cross-sectional elevational view of the instrument.

FIG. 3 is a partial, cross-sectional, left side elevational view of the preferred embodiment 10 illustrated in FIGS. 1–2B. Much of the electronics 300 illustrated in FIG. 14 is located on printed circuit boards 40 and 68, respectively. Circuit board 40 is supported by standoffs 42 mounted on mounting plate 44. Similarly, standoffs 66 support printed circuit board 68 and separate it from the main filter detector housing 64.

Figure 9A:
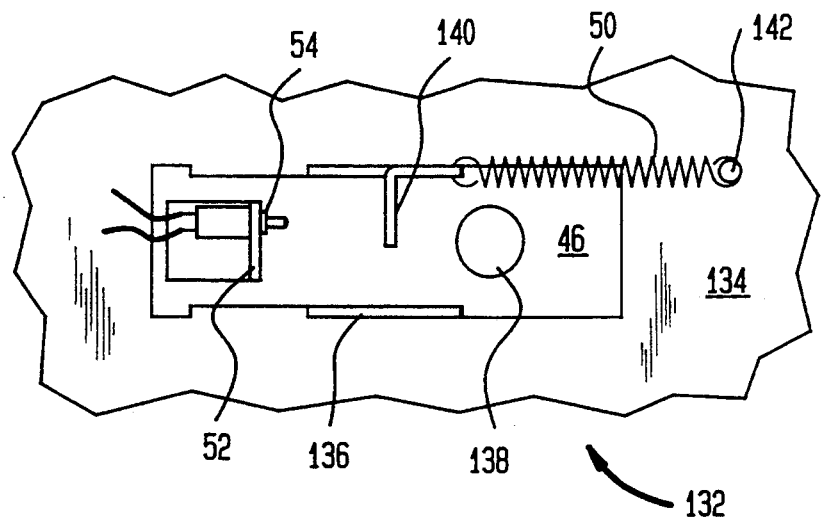
FIG. 9A is a rear elevational view of the viewport sub-assembly.
Figure 9B:
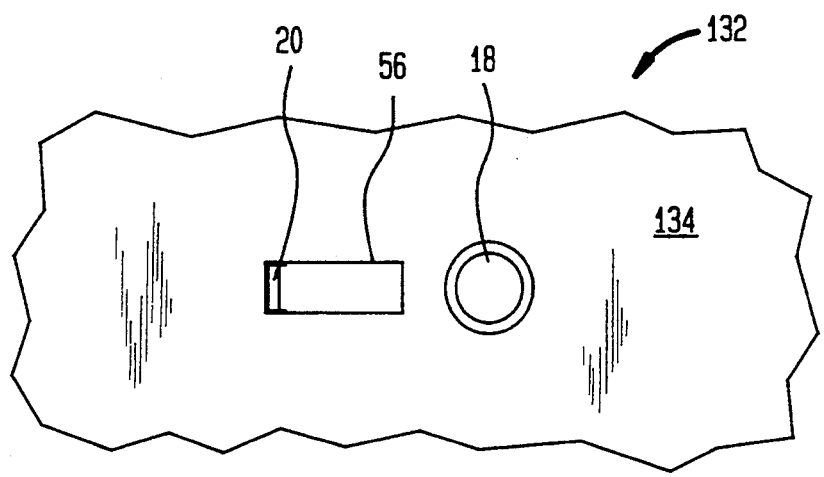
FIG. 9B is a front view of the viewport assembly illustrated in FIG. 9A.

Details of the sample viewport 18, also illustrated in FIGS. 9A and 9B, are also visible in FIG. 3. A slide plate 46 captured in a pair of guides 136 illustrated in FIGS. 9A and 9B, selectively covers or reveals viewing port 18. Viewing port slide plate 46 is controlled by pushing slider knob 20 sidewise against the influence of return spring 50. A limit switch, or microswitch, 54 is mounted on bracket 52. When the slider knob 20 is moved to the left in slot 56 as shown in FIG. 2A, a tab 140, carried by sliding plate 46, contacts microswitch 54 and turns on the krypton-filled tungsten lamp 84 of the lamp sub-assembly 82. This permits the user to view the sample 28 through the viewing port 18 which aligns with the apertures 80 in the color detector head assembly 64 and the apertures 104 and 226 in the annular aperture ring 94. When the user releases his or her finger from the slider knob 20, the spring 50 returns the slide plate 46 to its closed position, thereby occluding the viewing port 18 and automatically turning off the krypton bulb 84. The other end of the return spring 50 is attached to a spring post 142 illustrated in FIGS. 9A and 9B.

Figure 4:
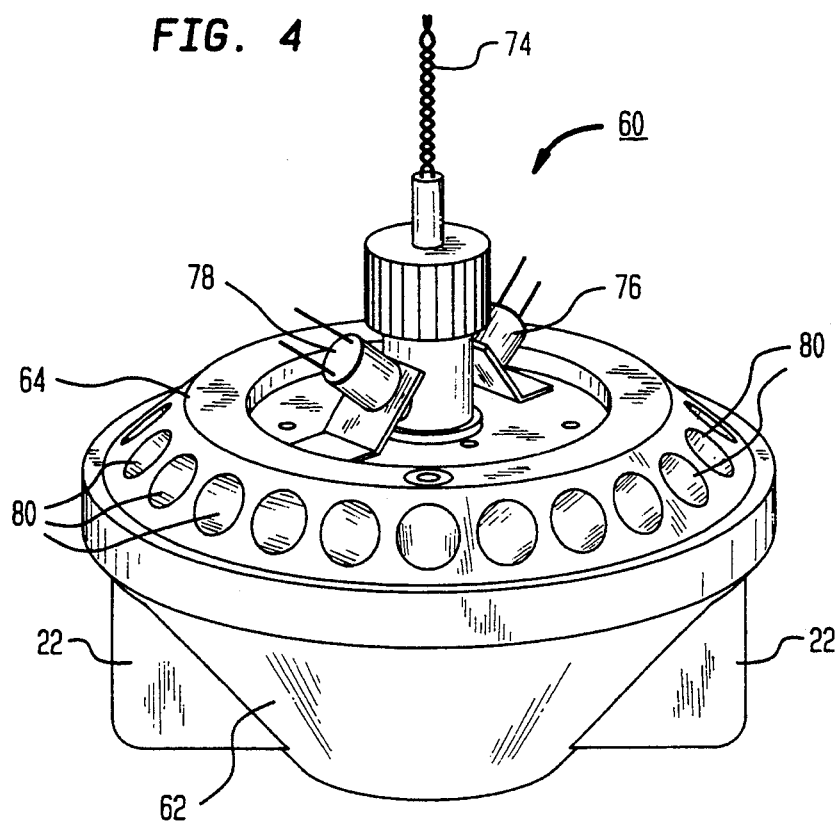
FIG. 4 is an exterior view of the color measurement head assembly.
Figure 5:
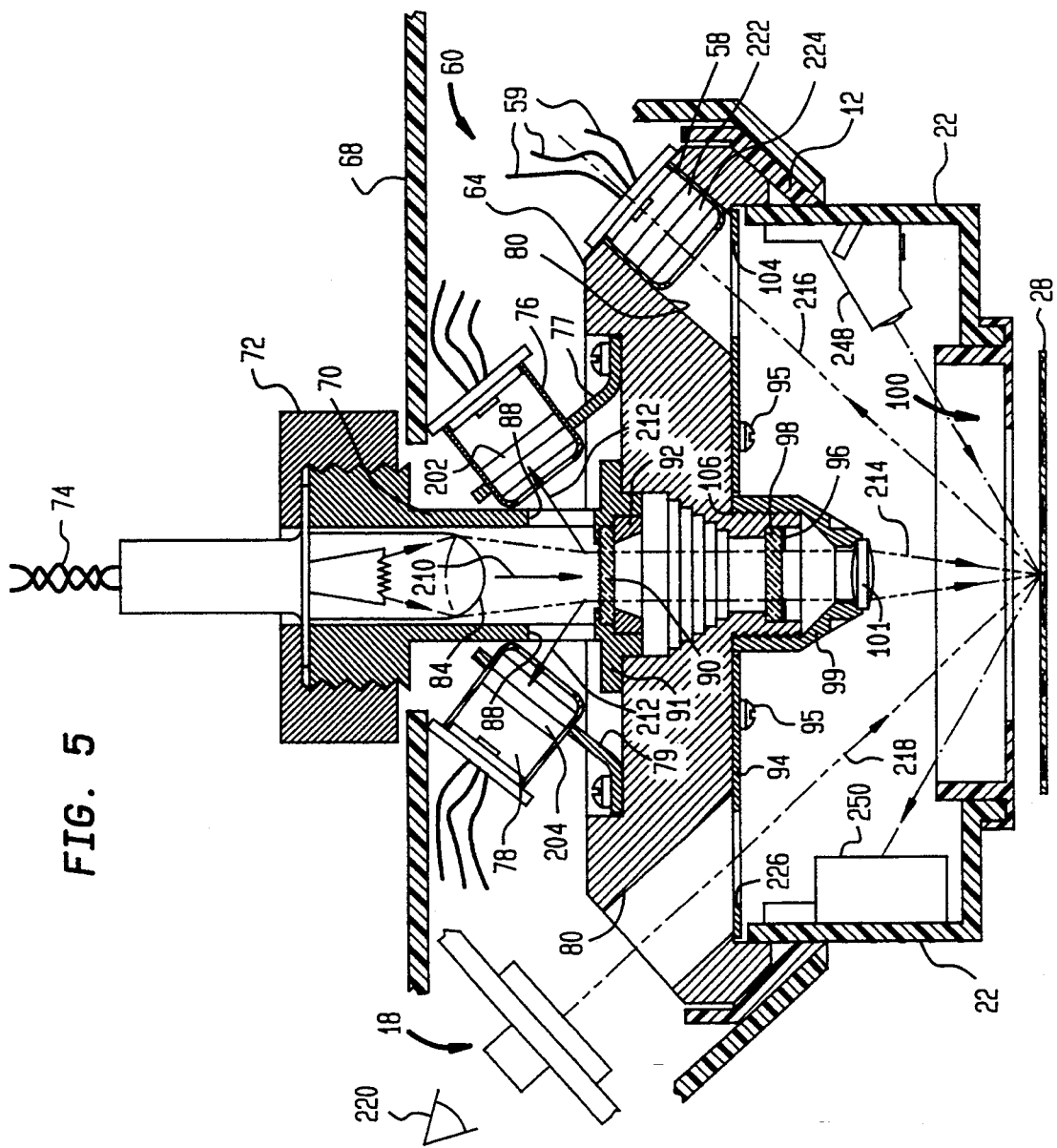
FIG. 5 is a cross-sectional view of the color and gloss measurement head assembly of FIG. 4.

FIG. 4 and FIG. 5 illustrate, respectively, exterior and cross-sectional views of the color head sub-assembly 60. The body of the color head sub-assembly 60 principally includes the main filter detector housing 64 which mates with the bottom conical housing 62. Twenty-two apertures, or holes, 80 are included in the beveled edge of the color detector housing 64. Twenty-one of the twenty-two holes accommodate, respectively, twenty-one narrow band filters 222 and related color photodiodes 58 each of which has a pair of leads 59 therefrom which connect to amplifiers 306a–306u illustrated in the schematic 300 of FIG. 14A. The remaining aperture 80 aligns with the sample viewing port 18 so that a sample 28 can be inspected by a user 220 when the viewport slide plate 46 is moved to the left.

Figure 6:
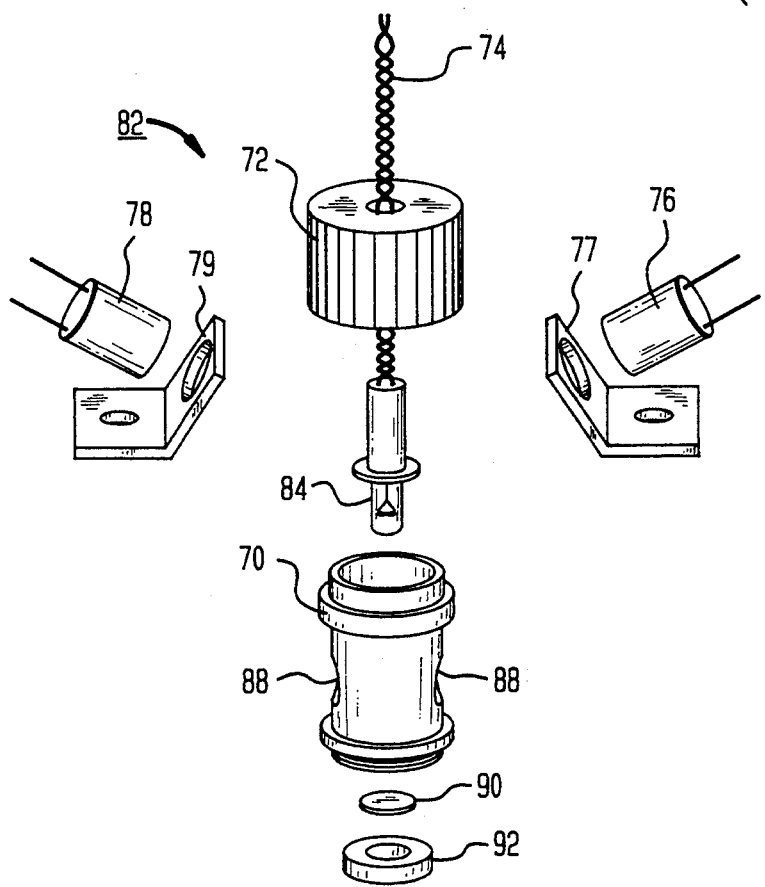
FIG. 6 is an exploded view of the lamp assembly.

The lamp sub-assembly 82, shown in further detail in FIG. 6, houses a pair of reference filter detectors 76 and 78. Reference filter detector 76 is mounted on bracket 77 to upper color housing 64 and measures light in the 400 nm range. Similarly, reference filter detector 78 is mounted by bracket 79 to color filter housing 64 and measures light in the 700 nm range. As shown in FIG. 5, the photodetector 76 includes an internal 400 nm filter 202. Similarly, the photodetector 78 includes an internal 700 nm filter 204. Photodiodes 76 and 78 are positioned adjacent apertures 88 in lamp housing 70 so that they can detect light that is reflected off of the ground glass diffuser 90. Diffuser 90 is held in position by a holder 91 which also houses a 5 mm aperture 92. A knurled lamp retaining nut 72 holds the krypton-filled tungsten lamp 84 in housing 70. A twisted cord pair 74 connects lamp 84 to a 5-volt power supply switch 346 illustrated in FIG. 14B.

Figure 8:
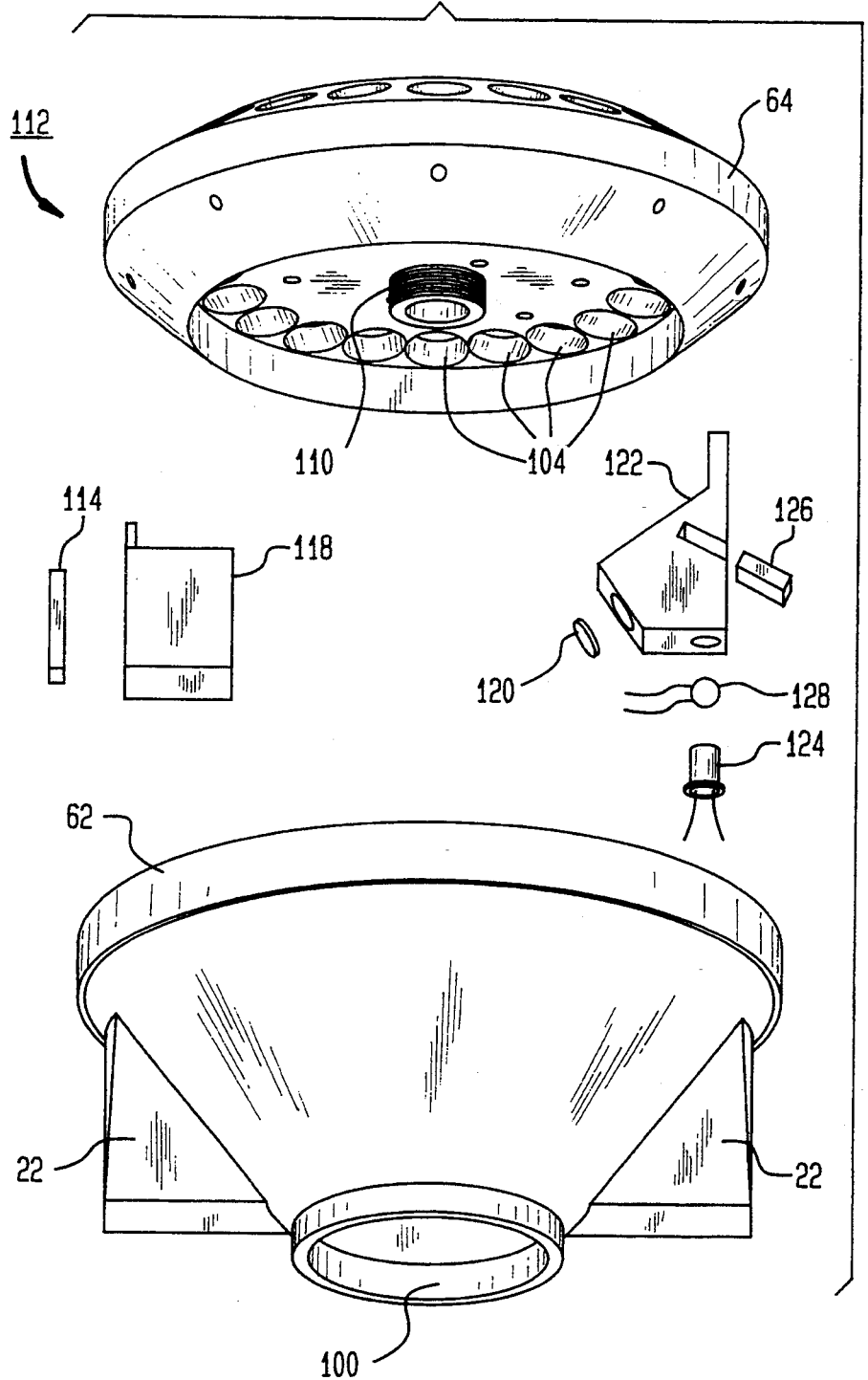
FIG. 8 is an exploded view of the gloss emitter and detector elements housed within the color head measurement assembly.

The bottom section of the color detector head 60, such as illustrated in FIGS. 4 and 5, can be further understood by referring to FIGS. 7 and 8. An annular aperture ring 94 is mounted to the underside of the upper color detector housing 64 and held in position there by two or more screws 95. Annular aperture ring 94 includes twenty-two outer apertures 104 that align with the color filter/detector holes 80 in the color detector housing 64. A central portion of the color detector housing 64 protrudes through the central aperture 106 in the aperture plate 94 and threadably receives a removable lens holder 99. Lens holder 99 supports a focusing lens 101 which can be employed to narrow the width of the light beam emitted from krypton-filled tungsten bulb 84. Alternatively, the lens housing 99 can be unscrewed and removed, thereby illuminating a larger portion of the sample 28. The ability to easily and selectively modify the amount of light shining on a sample 28 is considered an important improvement over the prior art in the context of color/gloss measuring instruments. The portion of the color detector housing 64 that protrudes through the aperture 106 also houses a daylight, blue glass colour conversion filter 98 and a 4 mm aperture 96. As seen in FIG. 7, the lower conical section 62 of the color head assembly 60 includes a lower, circular sample aperture 100 and a pair of gloss detector protrusions 22 which include cavities 102 to hold the gloss emitter and detector sub-assemblies 112 and 118 illustrated in further detail in FIGS. 8 and 13B. The upper color detector housing 64 also includes a central aperture 110 for threadably receiving the lamp sub-assembly 82 illustrated in FIG. 6. Threaded screw holes 108 make it possible to mount the printed circuit board 68 to the optical head 60.

Figure 10:
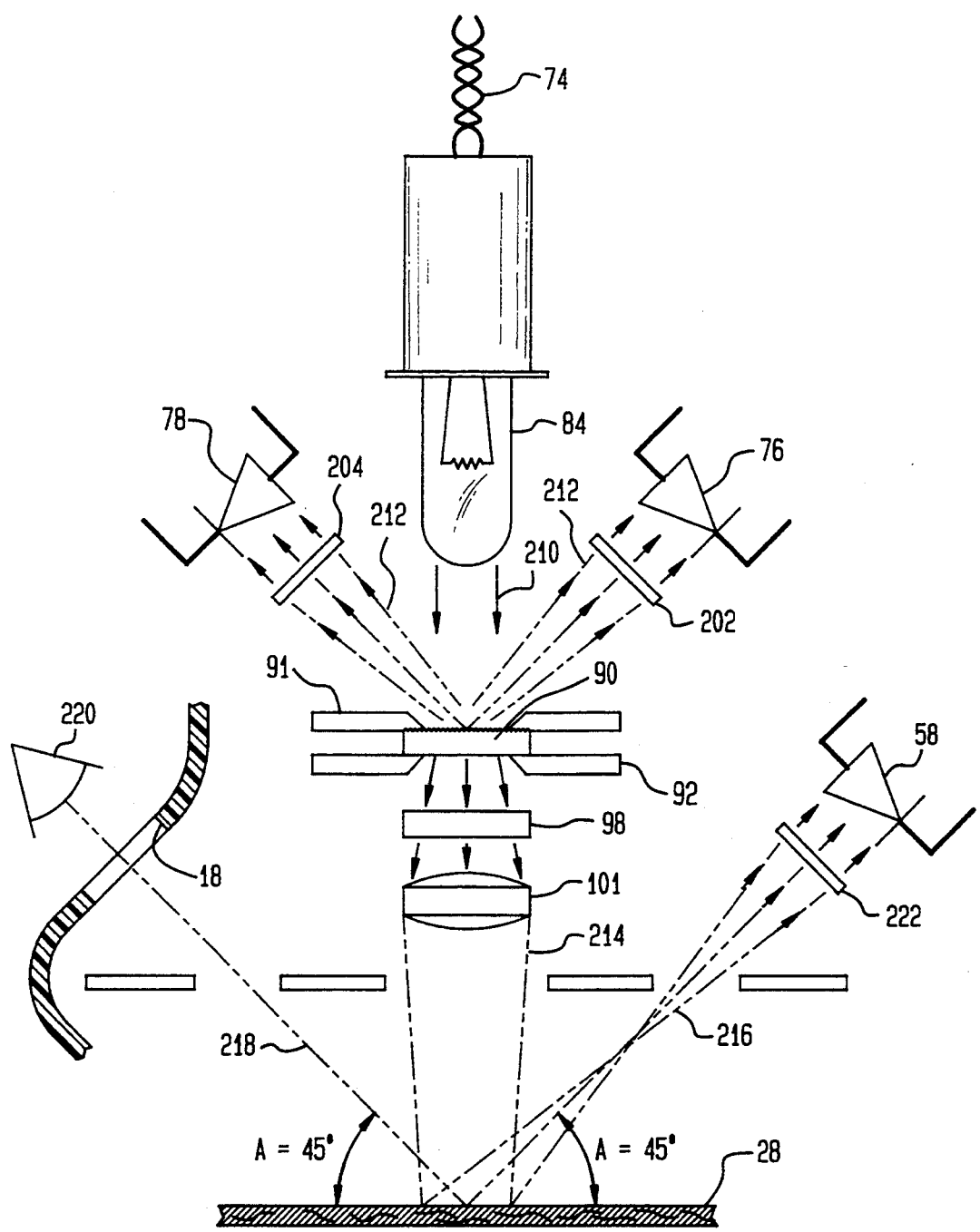
FIG. 10 is a schematic representation of the relationship between the light source, the two lamp reference diodes, a color photodiode and the sample viewport.

FIGS. 5 and 10 illustrate the manner in which the light generated by krypton-filled tungsten lamp 84 is distributed throughout the color detector sub-assembly 60. A broad spectrum light beam 210 generated by krypton lamp 84, initially impinges upon partially reflective ground glass diffuser 90. A portion of the light 212 is reflected, respectively, to feedback detectors 76 and 78 which detect light at the opposite ends of the visible spectrum at 400 and 700 nm. The remaining portion of the light beam 214 passes through the ground glass diffuser 90, a 5 mm aperture 92, daylight blue glass color conversion filter 98, a 4 mm aperture 96, and lens 101 to impinge upon the surface of color sample 28. Light beam 214 is then reflected as light beam 216 at a 45° angle from the normal to the twenty-one different color filters 222 and photodetectors 58 mounted in the color detector housing 64. Similarly, another portion of the light beam is reflected via path 218 through the color viewing port aperture 226 in aperture plate 94 and through aperture 80 in housing 64 and finally through the viewing port 18 to the eye of the user 220.

Figure 13A:
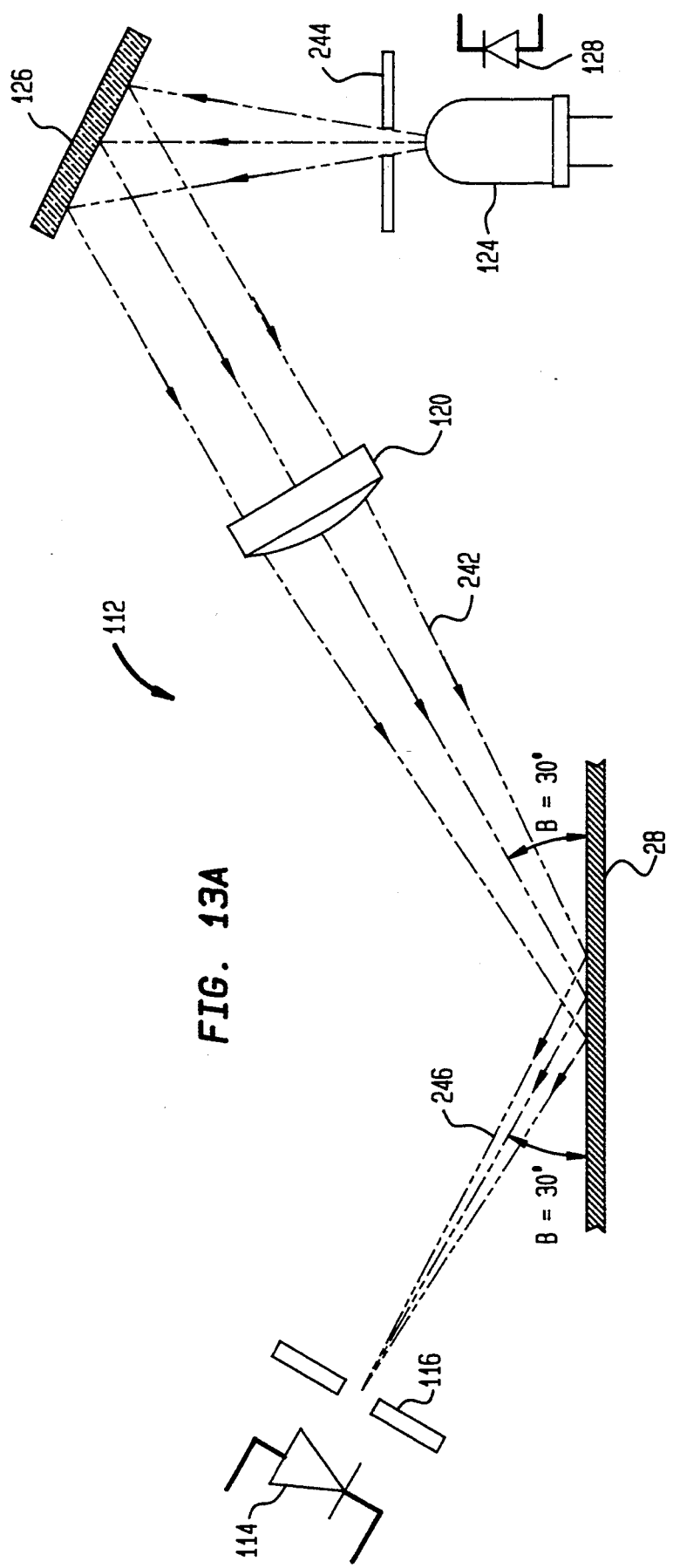
FIG. 13A is a schematic illustration of the gloss measuring sub-system and, in particular, illustrating the geometrical relationship between the gloss light emitter and the gloss detector.
Figure 13B:
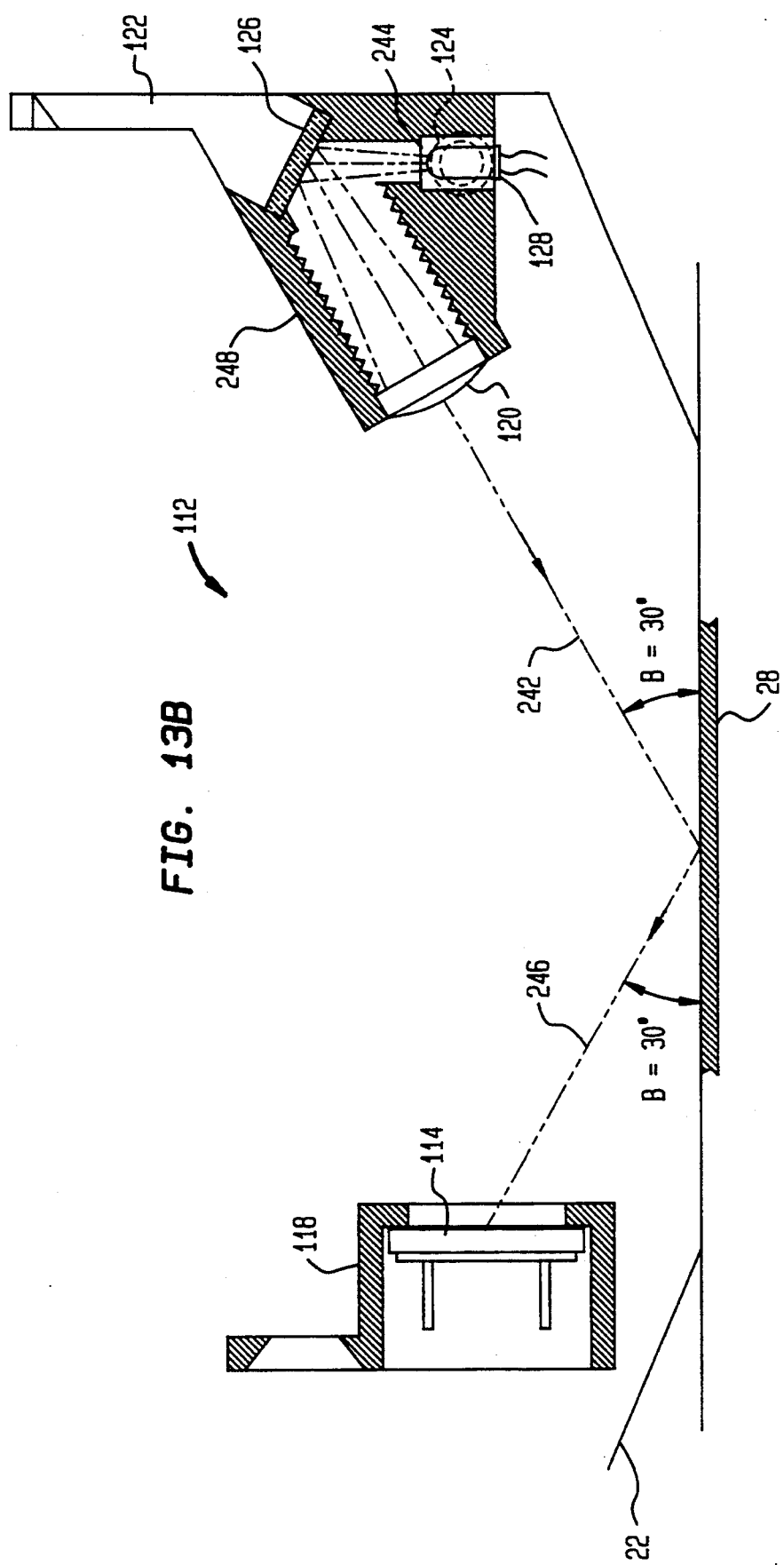
FIG. 13B is a cross-sectional detail mechanical view of the gloss detector sub-system illustrated in FIG. 13A.

The details of the gloss detector sub-assembly 112 are shown in FIG. 8 and also in related FIGS. 13A and 13B. The detector portion of the gloss detector sub-assembly 112 includes a large-area photodetector 114 and a detector aperture 116 supported by and mounted within a gloss detector housing 118 which fits within one of the cavities 102 in one of the protrusions 22 of the lower conical housing 62. The emitter portion of the gloss detector sub-assembly 112 comprises a lens 120, a gloss emitter housing 122, a light emitting diode (LED) 124, a rectangular aperture 244 for defining the beam spread of one LED 124, a mirror 126 for reflecting the light from the LED 124 and a gloss feedback detector 128 for comparing the light emitted by diode 124 with the light received by the large-area photo detector 114. The emitter housing 122 and its associated parts 120, 244, and 124-128, are received in the other cavity 102 in the other protrusion of the lower conical housing 62. As shown in FIGS. 13A, a light beam 242 generated by LED 124 passes through rectangular aperture 244 and is reflected off of the front surface of mirror 126 and is focused via lens 120 onto the surface of the color sample 28 at an angle $B=30°$ with respect to the measurement plane. A portion of the light is reflected as gloss illumination 246 which is focused onto detector aperture 116 and passes on to the surface of the large area photodetector 114. Since gloss is a measurement of the ratio of incident light to reflected light, it is necessary to detect the light emitted by LED 124 by the gloss reference photodiode 128 and compare that to the light received by the large area photodetector 114. Additional structural details of the gloss detector geometry 240 are shown in FIG. 13B. The light 242 from the LED emitter diode 124 passes through an aperture 244 before it impinges upon the surface of mirror 126. The reflected light beam 242 passes through lens 120 which is held in position by the gloss emitter housing 122. A small hole adjacent to LED 124 permits the gloss feedback detector 128 to sample the light from the LED 124. The emitted light 242 impinges the surface of the color sample 28 at an incident angle $B=30°$ from the measurement plane and is reflected at a similar angle $B=30°$, but diminished by the gloss factor, as beam 246. Beam 246 passes through aperture 116 supported by the detector housing 118 and impinges upon the surface of the large area photodetector 114.

Details of the viewport sub-assembly 132 are shown in FIGS. 9A and 9B. FIG. 9A is a rear view of the viewport sub-assembly 132 and FIG. 9B is a front view thereof. The viewport sub-assembly 132 is carried on mounting plate 134 which includes the view aperture 18 therein. The viewport slide plate 46 is captured by a pair of guides 136 which surround opposite edges of the slide plate 46. Slide plate 46 also includes an aperture 138 which selectively aligns with the viewing aperture 18 in the mounting plate 134 when the slide plate 46 is drawn sideways. Spring 50 is attached at one end to a spring post 142 mounted on plate 134 and at the other end to a tab 140 carried by the sliding plate 46. Spring 50 normally biases the slide plate 46 into the closed position so that apertures 18 and 138 are not aligned, thereby preventing stray light from impinging upon the sample 28 through the viewport Microswitch 54 is mounted on bracket 52 carried by mounting plate 18. 134. Slide plate 46 can be moved leftward, when the instrument 10 is seen by the user, by pushing slider knob 20 to the left. Knob, or tab, 20 is attached to the slide plate 46 and protrudes through the front of the mounting plate 134 so that it rides in slot 56.

When the instrument 10 is not being used, the bias of spring 50 draws the slide plate 46 to a normally closed position such that the viewing aperture 18 is shut. If the user wants to take a look at the sample 28 through the viewport 18, he or she merely pushes knob 20 to the left, causing it to ride across guide slots 116 against the load of spring 50. When the knob 20 reaches its far left hand extreme, the view aperture 18 is aligned with the aperture 138 in slide 46. This allows the user 220 to view the sample 28 through the viewport 18 and the associated aperture 226 in plate 94 as illustrated, for example, in FIGS. 5 and 10. Simultaneously, the tab 140 riding on the sliding plate 46, impinges microswitch 54 causing its internal circuit to close. This sends a signal to the microcontroller 314, shown in FIG. 14B, which in turn causes the krypton-filled tungsten lamp 84 to turn on. Therefore, the color sample 28 is automatically illuminated whenever the user pushes the knob 20 to the extreme lefthand position which, of course, permits the user 220 to view the sample 28 under the same lighting conditions as would be employed when the color detector sub-assembly is operated.

Figure 11:
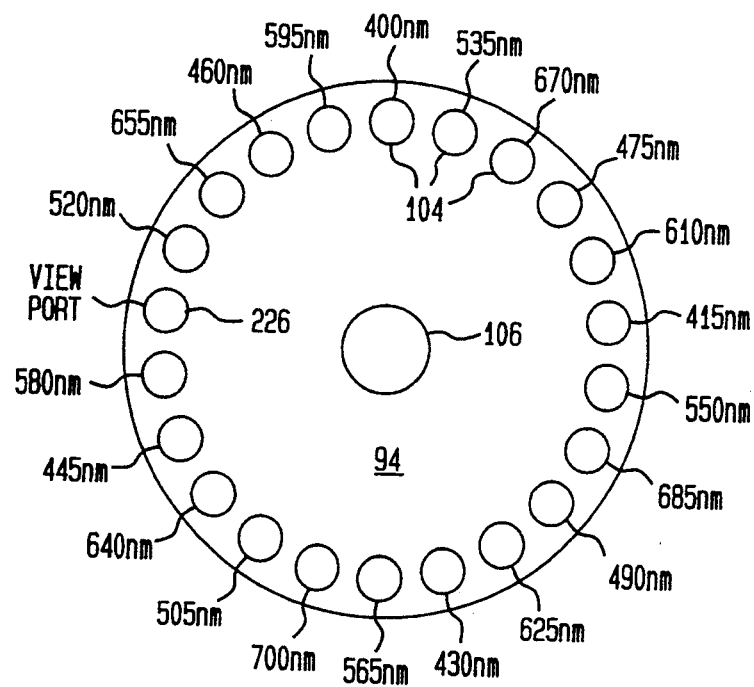
FIG. 11 is a top plan view illustrating the geometric arrangement of the twenty-one color filters and the viewport operative with respect to the annular aperture ring and showing how the peak frequencies measured are offset by five apertures from each other.

FIG. 11 is a top plan view of the annular aperture ring 94 showing the central hole 106 and the twenty-two outer apertures 104 therein. One of the outer apertures 104 comprises the viewport aperture 226. As shown in FIG. 11, the twenty-one photodetectors 58 and their associated narrow band filters 222 are organized to detect light in the 400–700 nm range at 15 mm intervals. They are also staggered in an organized fashion so that any intrinsic bias in the color detector/filter system will be balanced out. According to the preferred embodiment 10, each subsequent filter interval is located 5 apertures 104 away from its nearest neighbor in a clockwise fashion. Accordingly, the 415 nm detector/filter aperture is located 5 apertures 104 away from the 400 nm detector/filter aperture and, similarly, the 430 nm aperture 104 is located 5 apertures 104 in a clockwise direction away from the 415 nm aperture, and so on.

Figure 12:
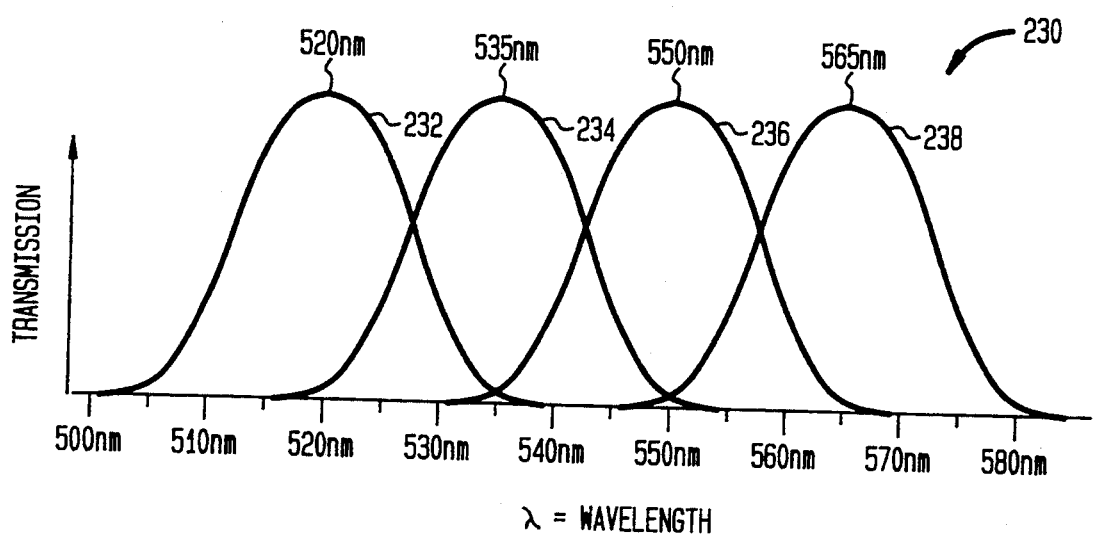
FIG. 12 illustrates the overlap of color wavelengths measured at 15 nm intervals over the range of 400–700 nm.

FIG. 12 illustrates a family of transmission curves 230 that illustrate that there is some overlap between adjacent 15 nm filter intervals. Shown in FIG. 12 are the 520 nm curve 232; the 535 nm transmission curve 234, the 550 nm transmission curve 236 and the 565 nm transmission curve 238. The curves 232–238 overlap sufficiently to guaranty that there are no significant gaps in between the 15 nm intervals, however, they do not overlap so much as to significantly reduce the resolution of the instrument 10.

Figure 14B:
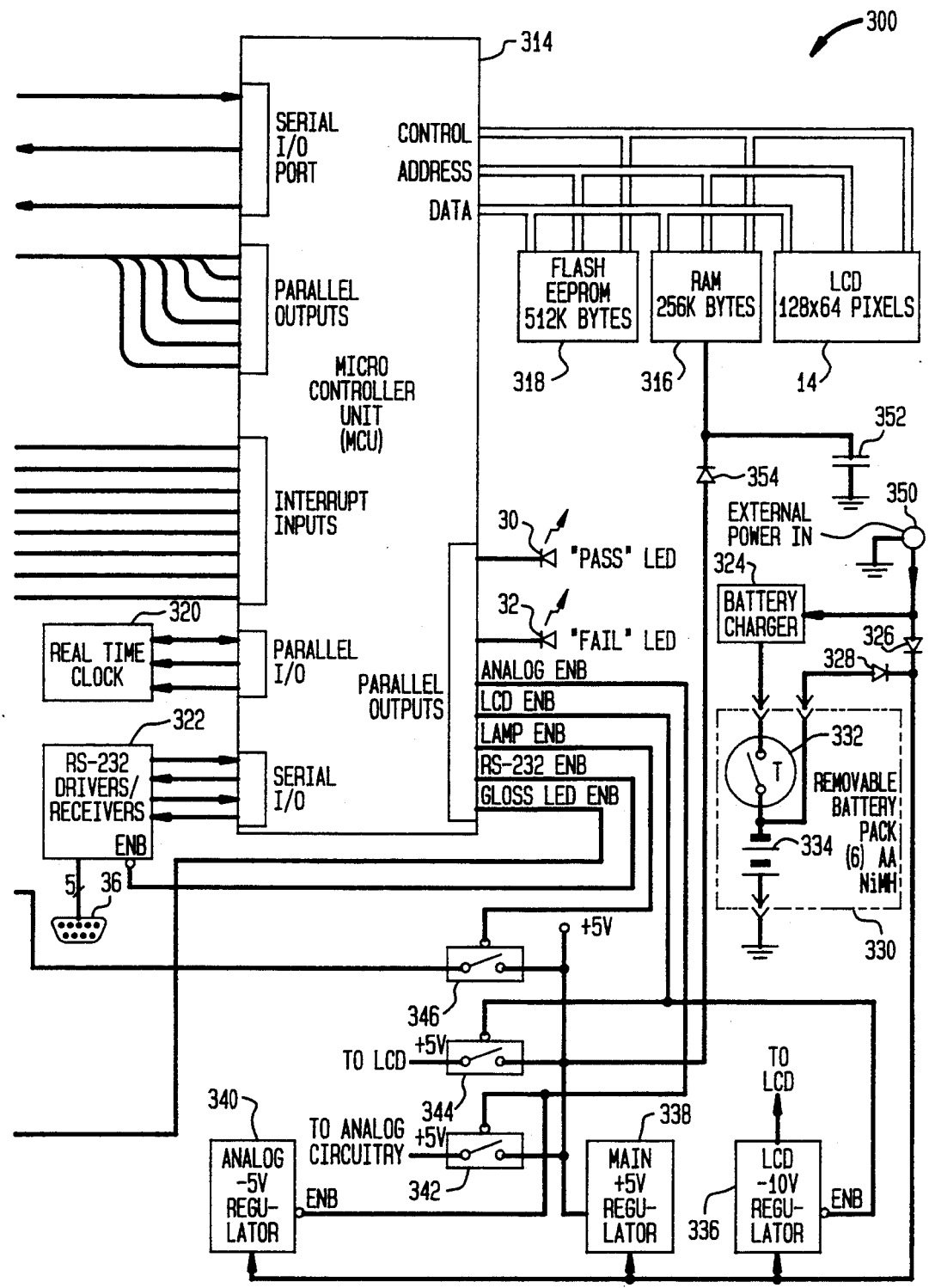

FIGS. 14A and 14B illustrate the electronic components that comprise the remainder of the instrument 10. Reflected light 216 impinges on twenty-one different narrow band color filters $222a$–$222u$ separated from each other and staggered according to the arrangements illustrated in FIGS. 11 and 12. Light rays transmitted through filters $222a$–$222u$ are detected, respectively, by photodetectors $58a$–$58u$ and amplified by amplifiers $306a$–$306u$. The output from amplifiers 306A–306H are fed to 8 to 1 multiplexor $306a$. Similarly, the outputs from amplifiers $306i$–$306p$ and $306q$–$306u$ are multiplexed by 8 to 1 multiplexors $308b$ and $308c$, respectively. The outputs from multiplexors $308a$–$308c$ is amplified by amplifier 310 and digitized by a 16 bit analog-to-digital converter 312 whose output is connected to the serial input/output port of microcontroller unit (MCU) 314. The MCU 314 preferably comprises a Motorola model MC68HC16Z1 microcontroller.

Reflected light 212 from ground glass diffuser 90 is filtered by 400 nm filter 202 and 700 nm filter 204 and detected, respectively, by color reference diode 76 and 78. The outputs of color reference diodes 76 and 78 are amplified, respectively, by amplifiers $306v$ and $306w$, the outputs of which form two inputs to the 8 to 1 multiplexor unit $306c$. Also, gloss reflection 246 is detected by detector 114 and amplified by amplifier $306x$ which also comprises another input to the 8 to 1 multiplexor $306c$. The outputs from the color reference channels and the gloss channels are subsequently amplified by amplifier 310 and digitize by A to D converter 312 and form another input to MCU 314. The gloss feedback detector 128 produces an input to amplifier $306y$, the output of which is connected directly to the 16 bit A to D converter 312.

The MCU 314 is driven according to instructions and information stored in 256K byte RAM 316 and flash 512K byte EEPROM 318. A real time clock 320 provides day, date and time of day. MCU 314 is capable of making very sophisticated and accurate measurements of appearance. In particular, it is capable of performing super ellipsoidal measurements similar to those described in pending U.S. application Ser. No. 07/900,564 entitled COLOR TOLERANCING SYSTEM EMPLOYING FUZZY LOGIC by Kevin B. Kern and David L. Alston. The output from MCU 314 is provided by LCD 14 or by pass/fail LEDs 30 and 32, respectively. A set of eight switches 16 provide instructions to the MCU. Six of the switches 16 are located on the front as illustrated in FIG. 2A and a seventh, also located on the front, comprises the microswitch 54 controlled by the viewport slide knob 20. The eighth switch 16 comprises the rear measurement initiation button 38 ("MEAS #2") visible in FIGS. 2B and 3 which is redundant with respect to the front measurement button ("MEAS #1"). The rear RS 232 9 pin port 36 is connected through RS 232 driver/receiver circuit 322 which is connected to another serial input/output port of MCU 314. Gloss lamp 124, whose output provides the input to detectors 114 and 128, is driven by LED driver 348 which is directly controlled by MCU 314. Krypton-filled tungsten lamp 84 is controlled by switch 346 which in turn is controlled by MCU 314. The other input to switch 346 is connected to the main +5 volt regulator 338. The LCD 14 is controlled by switch 344 which is connected to the main +5 volt regulator 338. The main +5 volt regulator 338 is also connected via diode 354 to 256K byte RAM 316. A 0.1 farad super Cap capacitor 352 supplies power during power off periods to the RAM 316 is connected between diode 354 and the 256K byte RAM 316. A −10 volt regulated power supply 336 is connected to LCD switch 344 and selectively provides power to the LCD 14. The analog circuits are powered by a −5 volt analog power supply 340 which is connected via switch 342 to the MCU 314 and the analog circuitry. External power may be supplied to the circuitry 300 through external power input port 350. External power input preferably comprises a 12 volt source. That power may go directly through diode 326 to power the circuit 300. Alternatively, the power may go to a removable battery pack 330 which comprises six AA NiMH batteries. The removable battery pack 330 includes an internal thermal switch 332 and the batteries 334. Removable battery pack 330 is placeable within the compartment protected by cover 26 illustrated in FIG. 3.

The instrument 10 just described with reference to FIGS. 1–4B operates in the following manner.

The instrument 10 is, according to the preferred embodiment, a portable colorimetric spectrophotometer with an integral gloss meter which permits it to make accurate spectrophotometric, colorimetric, reflection densitometric, brightness, whiteness, and yellowness measurements. The instrument 10 used a ruggedized, krypton-filled tungsten bulb 84 which is pulsed for approximately 0.7 seconds to generate sourced illumination of the color sample 28 for its non-gloss spectrophotometric functions. Light 210 from lamp 84 is collimated by the lamp itself and strikes the ground glass diffuser 90 at an angle that is perpendicular to diffuser 90 as illustrated in FIGS. 5 and 10. Diffuser 90 is apertured to 5 mm windows on both of its sides. The top side of diffuser 90 reflects light diffusely as beams 212, some of which is gathered by the two separate reference filter/detector pairs 76 and 78 which form the basis of the reference channel in a pseudo-dual beam system. Diffuser 90 also scatters and passes most of the lamp's light 214 through a second aperture 96 below it. This bottom light, defined by lower aperture 96, is then transferred to the sample plane through focusing lens 101 when small area samples (for example, 4 mm diameter) are measured. Alternatively, lens 101 can be removed by unscrewing lens holder 99 which permits illumination of a larger spot when it is desired to measure larger samples (for example, approximately 16 mm diameter). Color sample 28 is preferably located right in the bottom aperture 100 of the conical outer casing 62. Focused light 214 or direct light 210 falls perpendicularly on the surface of color sample 28 and the diffuse light is reflected off as beams 216 or 218 at angles between 40° and 50° (nominally 45°). Reflected light 216 passes through a set of twenty-one annularly arranged narrow band interference filters 222a–222u. Annular ring 94, which contains twenty-two separate apertures 104 and 226 limits the collection angle to 45° plus or minus 5°. Light passes through the interference filters 222a–222u at an angle that is perpendicular to their front surfaces. The admitted light then strikes normally each of the twenty-one different color detectors 58a–58u. This information is multiplexed by multiplexors 308a–308c, amplified by amplifier 310, converted from an analog to a digital signal by converter 312 and fed to MCU 314 as illustrated in FIG. 14A. The twenty-one filter/detector pairs 222a/58a–222u/58u together act as a twenty-one channel spectrometer as each filter allows a different region of the visible spectrum between 400–700 nm to pass through it. The twenty-one filter peak transmission wavelengths are nominally 400 nm, 415 nm, 430 nm, and so on up to 700 nm. Each filter 222a–222u has a Gaussian pass band shape (transmission vs wavelength) and a full-wave half-maximum bandwidth of approximately 20 nm as illustrated in FIG. 12. The pass band shape in conjunction with the overlapping nature of the filters 222a–222u allows the instrument 10 to model the colorimetric response of the human eye very accurately with no missing regions in the spectrum. In other words, as shown in FIG. 12, there is a 15 nm pitch between adjacent wavelengths and a bandwidth of 20 nm. In order to compensate for non-uniform surface samples 28 (such as corduroy textiles), filters 222a–222u which are adjacent in wavelength domain (e.g., 430 nm and 445 nm) and are geometrically placed 81.8° apart azimuthally as shown in FIG. 11. This achieves the same result as placing filters in apertures 104 which are five apertures 104 removed from each other in a disk that has twenty-two apertures 104 and 226 therein at equal intervals. In other words, 360°/22×5=81.8°.

Twenty-one narrow-band light beams are converted to electrical currents proportional to the light intensities by the twenty-one photodetectors 58a–58u. Each detector 58 has a current-to-voltage preamplifier 206a–206u associated with it which also produces output voltages proportional to the narrow-band light intensities. The twenty-one voltage output levels provide an input to one of three analog 8 to 1 multiplexors 308a–308c, the outputs of which are amplified by amplifier 310 and presented to analog-to-digital converter (ADC) 312 which turns the voltages into digital form for use by MCU 314. In addition to the twenty-one color sample channels, there are two reference channels which are composed of the 400 nm filter-detector-preamplifier set 202, 76 and 306v and the 700 nm filter-detector-preamplifier set 204, 78 and 306w. The reference channels are illuminated by the light 212 reflected from diffuser 90 and are treated exactly the same as the color sample channels illustrated in FIG. 14B. The purpose of the 400 and 700 nm color reference channels is to monitor variations in the incandescent light output of the krypton-filled tungsten bulb 84. This allows for a ratiometric correction of reflectance data that compensates for lamp intensity fluctuations as described below.

In many traditional, prior art dual-beam spectrophotometer instruments, there are typically two separate and identical spectrometers. Sub-assemblies of such prior art devices normally convert light into a set of discrete light intensity vs wavelength values. One set was traditionally used to measure light reflected off the sample being measured and the other used to measure light incident to the sample (often referred to as the "reference"). The two sets of numbers were then offset corrected (zero-light values are measured and used for base-line correction) and then ratioed (sample divided by reference) to compensate primarily for light intensity fluctuations, then secondarily for changes in electronic, mechanical and optical properties which affect both spectrometers equally (e.g., ADC drift, amplifier thermal drift, degradation of optical components in the illumination system, etc.).

The foregoing prior art technique is significantly different than the technique of the present instrument 10. In the present instrument 10, it is not necessary to measure twenty-one unique reference channels. That would require a significant increase in components and cost and a possible degradation in accuracy. Instead, the present instrument 10 uses two reference channel values, namely 400 nm, referred to as the "blue reference channel," and 700 nm, referred to as the "red reference channel," in order to produce a simulated twenty-one channel reference spectrometer. Each of the twenty-one measured wavelengths thus has determined for a unique reference value Ri according to the following relationship:

$R_i$=RedGain(i)×700 nm Reference Value+- BlueGain(i)×400 nm Reference Value+Offset(i)

where:
i=15 nm intervals for each color measuring photo-diodes from 400 nm through 700 nm;
RedGain(i)=amplifier gain in the red spectrum;
BlueGain(i)=amplifier gain in the blue spectrum;
Offset(i)=offset per color detector.

The values RedGain(i), BlueGain(i) and Offset(i) are mathematically determinable via a standard least squares fit optimization to actual sample reflectance data measurements made by the instrument 10. The Offset(i) term in the relationship for R(i) above is given by:

Offset(i)=Average Reference(i)−RedGain(i)×Average 700 nm Reference Value−BlueGain(i)×Average 400 nm Reference Value.

The average values referred to above are preferably determined during a lamp characterization procedure which is performed whenever the bulb is replaced, which may be annually or at any other regular interval. A series of consecutive measurements is made on a high reflectance white standard sample and BlueGain(i) and RedGain(i) values are calculated such that the cumulative sum of the squares error between the actual white tile sample readings and the reference value readings predicted by the relationship above for all measurements in this series is minimized. To compensate for long-term aging effects in the incandescent lamp 84, the Offset(i) value is recalculated during daily recalibration of the instrument 10, and the results are checked by the MCU 314 to determine if lamp recharacterization or replacement is necessary.

Once the pseudo reference spectrometer values have been generated, a dual-beam correction is applied to the measured sample data, thus providing very repeatable measurements at a cost significantly lower and at a greater accuracy than that associated with traditional prior art dual-beam units. This corrected spectral data is then processed according to known, prior art procedures to yield the spectrophotometric, colorimetric, reflection densitometric, brightness, whiteness, and yellowness data described above.

The instrument 10 also includes an ASTM D-523 compatible 60° dual-beam gloss meter sub-assembly 112 built into the unit. This consists of a green LED 124 whose emitted light 242 is monitored by photodiodes/-pre-amplifier circuit 128/306y which shares A-D converter 312 with the multiplexors 308a–c. Light 242 passed forward from LED 124 is apertured by aperture 244 to control its angular spread (per Standards ASTM D-523), reflected off mirror 126 (as a means of increasing path length without increasing the instrument's overall size), and focused via plano-convex lens 120 onto the sample 28 at a point equal in length to the path length from the lens to the sample being measured plus the path length from the sample to the gloss detector aperture 116. See FIGS. 13A and 13B. The gloss detector aperture 116 conforms to ASTM D-523, also. Reflected light 246 passing through aperture 116 strikes large area photodiode 114, and is amplified by preamplifier 306y, multiplexed by multiplexor 308c, and converted to digital signals by A/D converter 312 and presented identically to MCU 314 as previously described. Gloss detector values are ratioed to the gloss emitter monitored values to compensate for LED 124 intensity variations.

The electronic components 300 illustrated in FIGS. 14A and 14B include the onboard Motorola MC68HC16Z1 microprocessor 314 which includes 512K bytes of flash non-volatile memory 318 for program and calibration data storage and 256K bytes of RAM memory 316 backed up by a 0.1 Farad capacitor for customer data storage. Instrument 10 provides virtually all information necessary in a color quality control system and includes a superellipsoid based pass/fail test as described in copending U.S. application Ser. No. 07/900,564 entitled COLOR TOLERANCING SYSTEM EMPLOYING FUZZY LOGIC by Kevin B. Kern and David L. Alston, the entire contents of which are hereby incorporated by reference into this disclosure. It is also possible to provide machine instructions so that the instrument 10 is capable of color recipe correction and even color recipe formulation. Display 14 comprises a 128×64 pixel LCD which displays information for the user. RS-232 port 36 permits communication with other external peripheral devices such as personal computers, modems, bar code readers, etc. The front panel of the instrument as illustrated in FIG. 2A includes 6 user keys 16 ("menu"), a measurement initiation key ("MEAS #1") S1, S2, S3 and S4, and a viewport microswitch 54 which turns on the unit's lamp 84 at a very low intensity to allow the user 220 to look through the viewport 18 at the sample 28 to be measured. Additional microprocessor interfaces control power converter operation, lamp operation, gloss LED operation, ADC operation, multiplexor channel selection, and battery charging operations.

Primary power for the instrument 10 comes from rechargeable 7.2 volt NiMH battery pack 330. A main +5 volt level is generated by the external power supply 350 or the removal battery pack 330, and 2 other microprocessor-control +5 volt supplies (lamp power 338, and analog circuitry power 340). A −10 volts source 336 is also generated to bias the LCD 14, and −5 volts 340 is supplied for the analog circuitry. Each of these circuits is switched on and off as the microprocessor 314 instructs. The 0.1 Farad capacitor 352 supplies power to the on-board RAM 316 when no battery or external power supply is connected to the unit 10. Its capacity is several days.

Battery charging is performed whenever external power is supplied at port 350. The six AA NiMH batteries are charged at a C/10 rate for 16 hours, and switched to a steady-state C/40 level. Fast charging of battery packs (C/2 rate) can be accomplished external of the instrument 10 by plugging the battery pack 330 into a second connector on the external power supply.

Other accessories for the instrument can include a wrist-strap for camcorder-like holding, a hard handle for direct holding, a carrying case, a white calibration standard, a gloss calibration standard, a color tile for diagnostic use, an external power supply capable of charging battery packs externally, an RS-232 cable, etc. An optional bench top stand is also useful for static applications.

In summary, the invention incorporates a number of relatively unique features and advantages. First, it is capable of generating twenty-one pseudo-reference beam values based upon only two spectral reference readings. Second, its unique viewport mechanism allows the user to view the sample with a geometry identical to the unit's measurement illumination and viewing geometry. Third, its unique placement of filters at 81.8° with respect to each other, compensate for sample directional effects. Fourth, the unique incorporation of 20 nm FWHM Gaussian filters spaced 15 nm apart optimizes the instrument's determination of colorimetric standards. Fifth, the instrument 10 is capable of combining colorimetric data and gloss data to allow for (a) approximation of integrating sphere geometry readings and (b) pass/fail criterion based upon color and gloss values. Sixth, because fiber optics are not required, the size of the instrument can be significantly reduced.

While the invention has been described with reference to the preferred embodiment thereof, it will appreciated by those of ordinary skill in the art that various modifications can be made to the structure and operation of the invention without departing from the spirit and scope of the invention as a whole.

I claim:

1. A portable appearance measuring apparatus for measuring the appearance of a sample comprising:
   gloss measuring means for measuring the gloss of said sample, said gloss measuring means including a gloss measuring light source, a lens for focusing light from said gloss measuring light source onto said sample at a fixed angle B, a gloss detector aperture for receiving light reflected from said sample at said angle B, and a gloss detector for detecting light reflected off of said sample that passes through said gloss detector aperture, wherein said gloss measuring means detects gloss for light in the visible spectrum substantially within the range of 400–700 nm;
   color measuring means for measuring the color of said sample, said color measuring means including a color measuring light source, said color measuring means further including a housing located within said apparatus and including a sample port in the bottom thereof for placement over said sample, a plurality of apertures located in said housing and arranged substantially in an annular ring, and a plurality of color detector means each located respectively within said apertures in said annular ring in said housing, each color detector means detecting color at different wavelength intervals within said 400–700 nm range, wherein said color detector means are staggered within said annular ring so that adjacent color detector means measure color at a wavelength that is separated by at least one color measurement interval from its nearest neighbor;
   a sample viewing port including one of said apertures in said housing;
   a spring-loaded door for selectively opening and closing said sample viewing port;
   automatic light means operable by said spring-loaded door for illuminating said sample when said spring-loaded door is open;
   compensating means for compensating for variations in the output of said color measuring light source, said compensating means including an at least partially reflective member located between said color measuring light source and said sample, at least a first reference sensor for detecting light reflected from said at least partially reflective member, wherein said compensating means produces a compensating output at least partially responsive to said first reference source, said compensating means further including at least a second reference sensor for detecting said light reflected from said at least partially reflective member, wherein said compensating means produces an output in response to the reflected light measured by said first and second reference sensors, and wherein first reference sensor measures light in approximately the 400 nm range and said second reference sensor measures light in approximately the 700 nm range;
   analog-to-digital converter means connected to said color measuring means and said gloss measuring means;
   computer means attached to said analog-to-digital converter means;
   output means including a display means attached to said computer means;
   memory means connected to said computer means; and
   input means connected to said computer means for inputting data to said computer means,
   wherein said sample remains at substantially the same location when its appearance is measured by said color measuring means and said gloss measuring means.

2. The apparatus of claim 1 wherein said color detector means comprises approximately twenty-one color measuring photodiodes each of which measures color at approximately 15 nm wavelength intervals in the visible region between 400–700 nm.

3. The apparatus of claim 2 further comprising:
   means for generating a reference value $R_i$ for each of the twenty-one measured wavelength intervals to adjust for changes in said color measuring light source, wherein:
   $R_i$ = RedGain(i)×700 nm Reference Value + BlueGain(i)×400 nm Reference Value + Offset(i)
   and
   wherein:
   i = 15 nm intervals for each color measuring photodiodes from
   400 nm through 700 nm;
   RedGain(i) = amplifier gain in the red spectrum;
   BlueGain(i) = amplifier gain in the blue spectrum;
   Offset(i) = offset per color detector,
   and wherein said RedGain(i), BlueGain(i) and Offset(i) are determined by a least squares fit optimization of actual sample reflectance data measurements made by said color measuring photodiodes.

4. The apparatus of claim 3 wherein said apparatus is handholdable.

5. The apparatus of claim 4 further comprising:
   20 nm FWHM Gaussian filters spaced 15 nm apart between said sample and said color detectors.

6. The apparatus of claim 5 wherein said sample viewing port and said color measuring photodiodes are offset by an angle of approximately A=45° from the light beam that shines on said sample from said color measuring light source.

7. The apparatus of claim 6 wherein said light from said gloss measurement light source shines on said sample at said angle B of approximately 30° from the light incident on said sample from said color measuring light source.

8. The apparatus of claim 7 wherein said display means comprises a liquid crystal display (LCD).

9. The apparatus of claim 8 further comprising:
battery means for providing power for said apparatus;
battery holding means included in said apparatus for holding said batteries; and,
compartment means forming part of said apparatus for covering said battery holding means.

10. The apparatus of claim 9 further comprising:
a case for housing said apparatus, said case including a front portion including said liquid crystal display;
a set of function keys located on the front portion of said case, at least one of said keys including a first measurement actuation key; and,
a second measurement actuation key located on the back portion of said case.

11. The apparatus of claim 10 further comprising:
pass and fail visual indicator means located on said front portion of said case for indicating if a sample has passed or failed a combined color and gloss appearance test.

12. A portable appearance measuring apparatus for measuring the appearance of a sample comprising:
gloss measuring means for measuring the gloss of said sample;
color measuring means for measuring the color of said sample, said color measuring means including a color measuring light source;
a housing located within said apparatus and including a sample port in the bottom thereof for placement over said sample;
a plurality of apertures located in said housing and arranged substantially in an annular ring;
a plurality of color detector means each located respectively within said apertures in said annular ring in said housing;
a sample viewing port including one of said apertures in said housing;
a spring-loaded door for selectively opening and closing said sample viewing port;
automatic light means operable by said spring-loaded door for illuminating said sample when said spring-loaded door is open; and,
compensating means for compensating for variations in the output of said color measuring light source,
wherein said sample remains at substantially the same location when its appearance is measured by said color measuring means and said gloss measuring means.

13. A portable appearance measuring apparatus for measuring the appearance of a sample comprising:
gloss measuring means for measuring the gloss of said sample;
color measuring means for measuring the color of said sample, said color measuring means including a color measuring light source;
a housing located within said apparatus and including a sample port in the bottom thereof for placement over said sample;
a plurality of apertures located in said housing and arranged substantially in an annular ring;
a plurality of color detector means each located respectively within said apertures in said annular ring in said housing, wherein each color detector means detects color at different wavelength intervals within a 400–700 nm range, wherein said color detector means are staggered within said annular ring so that adjacent color detector means measure color at a wavelength that is separated by at least one color measurement interval from its nearest neighbor, and wherein each color detector means is separated by at least approximately 81.8° from a color detector means that is closest in detected color wavelength;
compensating means for compensating for variations in the output of said color measuring light source,
wherein said sample remains at substantially the same location when its appearance is measured by said color measuring means and said gloss measuring means.

14. A portable appearance measuring apparatus for measuring the appearance of a sample that lies in a plane comprising:
gloss measuring means for measuring the gloss of said sample;
color measuring means for measuring the color of said sample, said color measuring means including a color measuring light source;
compensating means for compensating for variations in the output of said color measuring light source;
a housing located within said apparatus and including a sample port in the bottom thereof for placement over said sample;
a plurality of apertures located in said housing and arranged substantially in an annular ring;
a plurality of color detector means each located respectively within said apertures in said annular ring in said housing; and,
an aperture plate including a central hole and a plurality of outer apertures therein which are aligned with the apertures in said housing, and wherein said outer apertures in said aperture plate all lie in a plane that is substantially parallel to the plane of said sample,
wherein said sample remains at substantially the same location when its appearance is measured by said color measuring means and said gloss measuring means.

* * * * *